United States Patent [19]

Patel

[11] Patent Number: 5,433,941

[45] Date of Patent: Jul. 18, 1995

[54] SOL GEL COMPOSITION FOR PRODUCING GLASSY COATINGS

[75] Inventor: Bipin C. M. Patel, Greenford, England

[73] Assignee: British Technology Group Limited, London, England

[21] Appl. No.: 142,486

[22] PCT Filed: Jul. 8, 1992

[86] PCT No.: PCT/GB92/01236

§ 371 Date: Nov. 29, 1993

§ 102(e) Date: Nov. 29, 1993

[87] PCT Pub. No.: WO93/00879

PCT Pub. Date: Jan. 21, 1993

[30] Foreign Application Priority Data

Jul. 12, 1991 [GB] United Kingdom ............. 9115153

[51] Int. Cl.⁶ .................... A61K 6/093; C09D 4/00; C09D 183/02

[52] U.S. Cl. ..................... 424/50; 106/35; 106/287.16; 433/217.1; 433/226; 433/229; 424/49; 424/52; 424/400; 514/835; 556/27; 556/40; 556/28

[58] Field of Search ............... 106/35, 287.16; 433/217.1, 226, 229; 424/400, 49, 50, 52; 514/835; 556/40, 27; 557/28

[56] References Cited

U.S. PATENT DOCUMENTS

| | | | |
|---|---|---|---|
| 3,751,275 | 8/1973 | Oken | 106/90 |
| 4,504,231 | 3/1985 | Koblitz et al. | 433/226 |
| 4,652,467 | 3/1987 | Brinker et al. | 427/426 |
| 4,673,354 | 6/1987 | Culler | 433/217.1 |
| 4,731,264 | 3/1988 | Lin et al. | 528/20 |
| 4,772,325 | 9/1988 | Kwan et al. | 106/35 |
| 4,801,399 | 1/1989 | Clark et al. | 252/315.01 |
| 4,842,888 | 6/1989 | Haluska et al. | 427/38 |
| 4,874,315 | 10/1989 | Featherstone et al. | 433/215 |
| 4,877,401 | 10/1989 | Higuchi et al. | 106/35 |
| 4,929,278 | 5/1990 | Ashley et al. | 106/287.12 |
| 4,983,381 | 1/1991 | Torres Zaragoza | 424/53 |
| 4,997,482 | 3/1991 | Haluska et al. | 106/287.16 |
| 5,013,624 | 5/1991 | Yu | 430/60 |
| 5,074,916 | 12/1991 | Hench et al. | 106/35 |
| 5,098,893 | 3/1992 | Franks et al. | 514/54 |
| 5,171,150 | 12/1992 | Levy | 433/226 |
| 5,328,645 | 7/1994 | Lin et al. | 106/287.34 |

FOREIGN PATENT DOCUMENTS

| | | |
|---|---|---|
| 0261593 | 3/1988 | European Pat. Off. . |
| 0381961 | 8/1990 | European Pat. Off. . |
| 1467979 | 2/1969 | Germany . |
| 4002726A1 | 9/1990 | Germany . |

OTHER PUBLICATIONS

JP 010129075 A, (Showa) see Derwent English abstract (WPI Acc. No. 89-189556/26).

*Primary Examiner*—Ronald W. Griffin
*Attorney, Agent, or Firm*—Nixon & Vanderhye

[57] ABSTRACT

Glassy coatings are made by curing in situ a coating of a sol gel of tetraethoxysilicon, water, alcohol, and the alkoxides of: Al, Ti and Na; or of Na and Zr.

The coating may be applied to teeth as a dental fissure sealant or varnish to protect restorations, or (if filled) as an inherently coloured cosmetic coating, or as a prophylactic coating.

30 Claims, No Drawings

SOL GEL COMPOSITION FOR PRODUCING GLASSY COATINGS

This invention relates to a sol gel composition for use in producing glassy coatings, to a process for producing a glassy coating using the composition, to a method for cosmetic colouring of teeth using the process and to a method for prophylactic protection of teeth using the process.

BACKGROUND OF THE INVENTION

Fissure sealants have been demonstrated as effective in reducing incidence of tooth decay and inhibiting decay even after it has started, but have not gained universal acceptance in general practice. These fissure sealants are understood to have relatively low durability, adhering to the tooth with a rather short half-life (5 years).

Sol-gels would not be considered for dental use, since the curing of sol gels is typically undertaken in a slow furnace, which would pose clinical difficulties. Japanese Patent Publication 1083671 (published 29 March 1989), in the name of Kobe Steel, proposes a calcium phosphate sol gel, but for coating artificial teeth to be subsequently embedded in the human body.

DESCRIPTION OF THE INVENTION

According to the present invention, a sol gel, xerogel or heat-consolidated gel composition comprises a hydrolysable silicic ester (such as silicon tetrahalide or tetraalkoxysilicon), a solvent (alcoholic or non-alcoholic), and alkoxides of a GpIA metal (e.g. sodium), and of any one, two or all of aluminium, zirconium and of a Gp VB or GpIVB metal (preferably titanium). Part of the silicic ester can be substituted by appropriate compounds of other non-metallic glass formers. Some of these compositions have been found to be usefully stable. The composition may further comprise water, which may however be supplied otherwise, e.g. by exposure to air. Preferred combinations of metal alkoxides are: (i) Al, Ti, Na; and (ii) Zr, Na. The metals (not counting Na) are preferably present in amounts up to 20%. Solid oxides e.g. fine neodymium oxide powder may be dispersed into the sol gel.

Preferably, the sol gel composition synthesis was characterised by an ageing step, during which moisture was admitted to the composition at a rate under 1% of the rate in free air. This controls the rate of hydrolysis and consequently of 'polymerisation' of the molecules of the composition without destabilisation, which rate can in principle be monitored via an increase in viscosity of the composition, or e.g. by infra-red spectroscopy, by differential scanning calorimetry, by thermogravimetric analysis, by nuclear magnetic resonance or by electron spin resonance.

Preferably, the sol gel, xerogel or heat-consolidated gel composition comprises a filler, such as laponite, zeolite, kaolinite or vermiculite, or preferably a filler In the form of flat plates such as talc or mica, or a mixture, optionally coated (preferably by chemical vapour deposition) with for example titanium dioxide, chromium oxide or ferric oxide or a mixture, the filler preferably comprising up to 30% by weight of the composition. Such materials are harmless if swallowed in the small quantities in which they might spall off. Other coating methods may also be used, alternatively or in addition, such as deposition of silane. This can promote adhesion and enhance mechanical properties. As silanising agents, compounds containing a glycidoxy organic group and a trimethoxysilyl group may be used, such as Dow Corning Z6040 (trade mark),

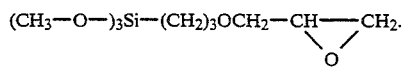

The mean filler particle size is preferably up to 3 μm (e.g. 0.1 to 2 μm) in one dimension and 5–100 μm in the other two dimensions. Where the latter dimensions are 5–20 μm, the filler preferably comprises from 20 to 30% by weight of the composition (i.e. before curing), and where those dimensions are 10–60 μm, the filler preferably comprises 10–20% by weight of the composition. Cross-laid fibres may be used. In the case of xerogel, which is 90 volume % air, a platey filler will improve its mechanical properties such that It could be used as an insulating material, or the cavities can be used as drug reservoirs, which will slowly release, on a tooth or otherwise.

The filler reduces the incidence of crazing in the cured sol-gel (not only in dental applications) by physically reducing the bulk of sol gel needed, thus making what there is of it more elastic. It also absorbs incident laser energy and re-emits it to the sol gel, accelerating the latter's curing. The filler also improves the abrasion resistance of the cured sol gel glassy coating. Given that the yield of glass from sol-gels is preferably about 5–10% by weight, and can be 0.1 to 1% or even less, the filler when present will in such cases thus be a major component of the product. In the case of mica, which tends to fall out of sol-gel suspension quite rapidly, it may be incorporated into the sol-gel when or immediately after the latter is made up; as the sol-gel 'polymerises', the polymers grow on the mica, improving its suspension and bonding, but as a precaution it may be advisable to shake it before use, or else the mica may be added to the sol gel at any later stage, e.g. immediately before use. On the other hand, a too-perfect suspension is to be avoided; as it is, the mica advantageously settles into pits and fissures, whither it is drawn by surface tension.

The hydrolysable silicic ester is preferably tetraethoxysilicon. The molar proportion of water:silicon may be (1 to 4):1, preferably (1½ to 3):1, for example 1½:1 or 2:1. Part of the Si, as already mentioned, can be substituted by appropriate compounds of other non-metallic glass formers along the lines of the teachings of for example Brinker and Scherer "Sol Gel Science" ISBN 0-12-134970-5, Academic Press 1990, pp 78–95 and Sowman at pp 162–165 in "Sol-Gel Technology for thin films (etc)" ISBN 0-8155-1154-X, Noyes Publications USA, 1988, about boron-based sol gels, as precursors for which such compounds as boron alkoxide, boric acid, boron nitrates or boron citrate, optionally esterified, are suggested. The solvent may comprise hydrophobic materials such as partly or wholly halogenated methane, e.g. CCl₄, or tetrahydrofuran, or diethylether, or hydrophllic materials such as Ketones e.g. acetone or alcohols e.g. ethanol optionally containing up to an equal volume of propanol (iso or n) preferably from ½ to ¾ volumes (e.g. 60 ethanol:40 propanol). The proportion of water plus solvent may be such that the composition yields 1–10 g silica per 100 g (the filler being included in the 100 g). In an alternative sol-gel preparation method, solvents (including water) may be absent and an intermediate solid may be converted into an applyable liquid sol gel composition by controlled exposure to atmospheric moisture.

A process for producing a glassy coating according to the invention comprises applying a sol gel composition e.g. as set forth above, to an object to be coated and curing the coating e.g. by flame (very miniature flames can be used in the mouth) e.g. butane flame heating, otherwise by radiation from the tip of a diathermy needle or preferably by laser, for example a $CO_2$ laser, with an energy input to the object of preferably 200 to 1000 $J/cm^2$ preferably applied at a rate which does not cause overheating leading to cracking or flaking of the film, such as under 4 W (more preferably up to 1 W) per $mm^2$, e.g. 0.2 to 0.8 W/mm, preferably for a duration of 1 to 4 (e.g. 2 to 3) seconds i.e. in the region $\frac{1}{2}$-3 $J/mm^2$. A $CO_2$ laser may be tuned to 10.6 μm as is most usual, or may be tuned to or near 9.6 μm (e.g. 9½–10 μm), which is most strongly absorbed by natural tooth. This is useful if it is desired to fuse (physically incorporate) the sol gel into the enamel, which also fuses, a procedure which requires high laser power outputs, and which is expected to make the enamel more resistant to caries. The pulse width and frequency can be varied to suit the thickness of the film to achieve good consolidation. This energy input is found to raise the tooth temperature by only 1°–2C., excess heat being removed by the blood supply to the pulp. An Nd:YAG 1.06 μm laser could be used, but needs a chromophore in the sol gel to absorb it. The coating as applied (before curing) may be up to 30 μm thick, preferably 1–10 μm e.g. 2–10 μm with filler and preferably 1–20 e.g. 5–20 μm without filler. The cured coating may be $10^{-2}$–$10^{0}$ μm thick without filler, but can be built up (to lengthen its lifetime) by multiple coating operations.

A method for cosmetic colouring of a tooth according to the invention comprises using the process set forth above, wherein the said object is the tooth. The tooth may have been treated with restorative material such as glass alkenoate cement, for which the present invention can be regarded as providing a protection. The sol-gel may include a pigment. The neodymium oxide powder suggested above imparts a remarkably evenly distributed blue colour to the glass. Alternatively, if a filler is present, preferably the filler is so formulated as to appear a tooth-like colour in the applied thickness. Alternatively, the tooth is stained cosmetically, and the stain retained by the applied coating. As a side-effect, prophylactic benefits may be obtained.

A method for prophylactic protection of a tooth according to the invention comprises using the process set forth above, wherein the said object is the tooth. The tooth may have been treated with restorative material such as glass alkenoate cement, for which the present invention can be regarded as providing a varnish. Preferably the filler is so formulated as to appear a tooth-like colour in the applied thickness. As a side-effect in that case, cosmetic benefits may be obtained. In all these methods, the option (explained above) of fusing the enamel, at least superficially, may be adopted.

Preferably the tooth is cleaned beforehand e.g. mechanically or by acid-etching.

The present invention provides a method whereby drugs may be released slowly, comprising allowing a coating produced by xerogel as set forth above and charged with the drug to ablate.

The two forms of product derived from sol-gel, viz glass and xerogel, differ in the physical organisation of their polymeric structures:

(i) Sol-Gel derived glass: A high density polycondensed $SiO_2$ lattice or network with minimal porosity.

(ii) Sol-Gel derived xerogel: A polymeric structure which is highly porous in the 100 nm range and of correspondingly low density, having trapped organic residues and being mechanically weak. The formation of a xerogel is a direct indication of sufificient hydrolysis to yield a useful glassy material. The deposition of a thin film from these sol-gels will depend upon dilution factor and nature of the solvents used. It Is important to note these sol-gels once synthesised will continue to undergo hydrolysis and condensation.

Defect free glassy films are important for adequate tooth protection, and require careful attention to two crucial stages in the sol-gel process once a continuous liquid coating has been applied:

(i) Sol liquid-to-gel transition
(ii) Consolidation of gel to glass.

Stage (i) needs to be slow which implies controlled rate of solvent loss, otherwise the shrinkage of resulting gel Is rapid and uneven leading to a fractured coating. The gel has to be partially dried and then given even surface heat treatment. Stage (ii), viz heat treatment, also needs to be carefully controlled, otherwise the film will crack and/or blister. The glass coating is vulnerable to cracking during heat treatment where shrinkage occurs, as density increases, mainly in the vertical direction and not the horizontal. Thin coatings that are less than ¼ μm generally do not suffer from cracking and have better mechanical durability. Following this finding, efforts to develop a sol gel glass having the same coefficient of thermal expansion as natural tooth were discontinued as unnecessary.

Using liquid spreading techniques likely to be available in ordinary clinical practice would however yield coatings on tooth surfaces having a thickness of approximately 1–20 e.g. 5–10 μm. (Applying a drop from a dropwise dispenser, it spreads across the tooth surface spontaneously.) As indicated above, the addition of inert fillers such as mica flakes is desirable; it permits thicker yet crack-free consolidated glass coatings and improves xerogel coatings.

Sol-gel derived coatings may be applied to:(i)
(i) Fissure sealing
(ii) Sealing marginal gaps arising from old restorations
(iii) Entire tooth crown surface protection
(iv) Root canal therapy, e.g. sealing tubules
(v) Lining freshly prepared cavities (blocking open tubules)
(vi) Protection of cavities freshly restored with filling materials.
(vii) Replacing the use of porcelain veneers for aesthetically coating discoloured enamel surfaces
(viii) Slow release of fluoride for topical application to tooth
(ix) Controlled release of drugs for example in the treatment of dentine hypersensitivity or periodontal disease, and
(x) Impregnation of porous structures for mechanical strengthening and other purposes e.g. drug release, enamel disorders and dental material improvement.

There are certain preferred ranges of compositions of the sol-gel. Considering atoms of Si, Na (or equivalent), Al, Zr and Ti (or equivalent), silicon preferably accounts for at least 30, more preferably at least 40%. Sodium is preferably under 50% (on an atomic basis again) such as 1–40%, more preferably 5–30%. Aluminium may be 5–15%, and titanium and/or zirconium and/or vanadium and/or niobium and/or tantalum 3–15%, more preferably 5–10%, and/or not exceeding one-sixth of the silicon. Silicon is desirable as a glass-former, and sodium should be limited as it makes the glass less resistant to acid.

EXAMPLES

The invention will now be described by way of example.

A multicomponent sol gel was prepared containing:
(Example 1): $Si(OEt)_4$, NaOMe and $Zr(O-n Pt)_4$
(Example 2): $Si(OEt)_4$, NaOMe and $Al(O-secBu)_3$ The synthesis conditions greatly affect the final properties, and in these Examples the preparation involved carrying out all reactions and mixing in a moisture-free atmosphere (glove box and/or a vacuum line apparatus with dry $N_2$ atmosphere). Any medically acceptable solvents could be used. All the alkoxides were made up separately in ethanol. Tetraethoxysilicate (TEOS, Si-$(OCH_2CH_3)_4$) was partly hydrolysed by adding a limited amount of water, ($H_2O:Si(OCH_2CH_3)_4=2:1$ moles) and maintained at 70° C. for 2 hours (normally at equimolar water is added). If the theoretical amount of 4 moles water per mole of TEOS (pH 6) is used, cosolvents such as ethanol with isopropanol will be found necessary. With gentle refluxing for a short time, such as 2 hours or less, a sol-gel should result stable at room temperature for at least 2 months and even longer at 0° C. Some of the Si—O—$CH_2CH_3$ groups became hydrolysed to Si—OH and ethanol.

First the sodium ethoxide (4.7 g) (dissolved in anhydrous ethanol) was added to TEOS (21.9 g) followed by 4.3 g Zr-propoxide (Example 1) both being in 17.5 g ethanol (anhydrous). A yellow/orange coloured liquid was formed. Example 2 was similar, with Al replacing Zr mole for mole.

After 24 hours the sol showed no sign of turbidity or any precipitation or gelling at room temperature. The sol-gel made in this way appeared to be stable for 6–12 weeks. Addition of a few drops of water (approximately 1 ml) to the sol-gel (approximately 3–4 ml) resulted in rapid gelling, with the formation of a light orange gel. The gel was left to dry out at room temperature leaving a pale yellow-orange xerogel.

The conversion of gel to xerogel at room temperature results only in partial hydrolysis of TEOS. Only a proportion of the expected $SiO_2$ was incorporated into the glass. The chemical composition of the xerogel was found by X-ray diffraction analysis to be $SiO_2$ 64%, $Na_2O$ 24% and $ZrO_2$ 12%.

Both yielded two types of coating, a xerogel incomplete conversion of metal alkoxide to oxide resulting in a low density highly porous (nm range pore size) material, and glass the coating consists of metal oxide in the form of a glassy lattice with negligible levels of metal alkoxide/residues.

The transformation or polymerization of the liquid sol gel to a gel state requires the loss of solvents and finally polycondensation to the consolidated glass state. This can be achieved by a hot air dryer or by infra-red laser absorbed by silica glass i.e. laser wavelength >2 $\mu m$, such as a $CO_2$ or Er:YAG or Ho:YAG (yttrium aluminium garnet) laser. The $CO_2$ laser may be tunable (rather than fixed at 10.6 $\mu m$) if it is desired to make use of the fact that absorption by natural enamel of radiation of $\lambda = 9.61$ $\mu m$ is many tens of times that at 10.6 $\mu m$. For lower wavelength lasers, a chromophore should be used to absorb the laser energy. To absorb the radiation of the latter, the sol gel included 1–5 weight % of a transition ion salt being any one or more of cupric nitrate, cupric sulphate, chromium (III) chloride, chromium (V) oxide and potassium permanganate, and an energy input of 100 $J/mm^2$ was required, too much for intra-oral use.

Using cw $CO_2$ laser (10.6 $\mu m$), conversion of gel to glass was complete, producing a coating which appeared to be totally resistant to 0.5M (usually only 0.02M is used for tests) of lactic acid even after 30 days. Normally only 0.02M concentration is used in conventional studies. $CO_2$ lasers have the property that their output is strongly absorbed by glass, virtually all the energy being absorbed within a thickness of 30 microns.

These sol gels have been modified by loading inert fillers to make Examples 3 and 4 respectively. Inert fillets such as "ceramic colours" of particle size 2–10 $\mu m$ (1–5 weight %) were used but tended to settle out of the sol gel with time. Metal chippings, flakes or flat scrapings could be used. Small particles of mica were successfully loaded and greatly improved the quality of the coating and its mechanical properties.

The mica, in plates 1–2 $\mu m$ thick and 10–50 $\mu m$ in the other two dimensions, was fully coated with a layer of $Fe_2O_3$, then a layer of $TiO_2$, or the other way round, or either one, which controlled the colour and is believed to have assisted bonding with the sol-gel (which itself bonds to natural tooth chemically rather than purely physically). It was found that the mica plates lay in place well, parallel to and adapting to the tooth surface. The various micas used are listed by particle size (diameter of flat surface) and chemical nature of their coating:

| Particle size | Coating Type | Appearance | % used by weight total | Coating Quality |
|---|---|---|---|---|
| 10–60 $\mu m$ | $TiO_2$ (Anatase) | Silver pearl | 15 | Good |
| 10–60 $\mu m$ | $TiO_2$ (Rutile) | Silvery | 15 | Good |
| 2–20 $\mu m$ | $TiO_2$ (Anatase) | Lustre satin | 30 | Good |
| 40–200 $\mu m$ | $TiO_2$ (Anatase) | Flash pearl | 10 | Poor |
| 40–200 $\mu m$ | $TiO_2$ (Anatase) | Shimmer pearl | 10 | Poor |
| 10–60 $\mu m$ | $TiO_2$ (Rutile) | Lilac pearl | 15 | Good |
| 10–60 $\mu m$ | $Fe_2O_3$ | Royal Gold | 15 | Good |
| 10–60 $\mu m$ | $Fe_2O_3$ | Bronze | 15 | Good |
| 10–60 $\mu m$ | $Fe_2O_3$ | Red | 15 | Good |

Mica is a naturally occurring alumino-silicate ($KAl_2(AlSi_3O_{10})OH$). Its surface even in the uncoated state is thought to become chemically bonded to the glassy matrix. The hydroxy groups take part in Mica—O—Si bond formation. Only a very thin covering of gel is present over and In between the mica plates, and this reduces the tendency of the glass resulting from the gel to suffer from stress-relief cracking.

The physical properties of mica, that is good thermal and electrical insulation, high mechanical resistance, and low coefficient of friction, may also contribute to the lack of sol-gel cracking. Furthermore, the mica plates or flakes are oriented parallel to the surface on which the thickness of the coating has been applied, and this will arrest crack propagation normal to the surface, since such a crack must suffer lengthy 'detours' around the mica plates i.e. fracture length has been greatly Increased.

The sol-gels were applied to air-dried mechanically cleaned (equivalent to sand blasted) tooth surface via an analogous method to dip-coating. One to three drops (approximately 100-300 μl) of the sol-gel were deposited on to the tooth surface, a single drop sufficing for the whole occlusal surface. The liquid was spread over the surface with a jet of compressed air or a chip syringe. This simple method generated a thin coat of liquid. Compressed air thinning serves three important functions:

(i) Sol-Gel was forced into small crevices, pits and fissures (ii) Excess sol Is removed leaving a very thin film of liquid on the surface (iii) Solvents are evaporated off and atmospheric moisture catalyses hydrolysis and condensation resulting In polymeric gel formation.

The liquid readily flowed and wetted all surfaces evaluated (acid etched/EDTA cleaned or unprepared enamel, dentine, amalgam, glass ionomer and composite restoratives).

The remaining solvents and water in the gel, after compressed air thinning, required to be carefully removed. The gel was dried with a hair dryer at an air temperature of 50°-60° C. or 60°-70° C. for 5-10 s. The specimens were moved back and forth in the hot air stream at an approximate rate of 3-5 cm/s (for a short distance into and out of the air stream). Typically, the applied dry-weight gel loading over the surface was 7-13 μg/mm$^2$, equivalent to a consolidated coating thickness of the order of 101 μm.

Drying the gel further induces hydrolysis and condensation and the silica-oxygen system progresses to a glassy state.

The coating became semitranslucent, tacky and "gel-like". This gel state was the result of hydrolysis and condensation; with large "—O—Si—O—" polymer unit formation. If the gel was allowed to dry out at room temperature or at 37° C. for at least 5-10 minutes it formed a xerogel having a porous structure with incomplete hydrolysis and condensation of Si—OH and Si—O—CH$_2$CH$_3$ groups. The xerogel coating appeared to be continuous, with some degree of fracture, and was transparent/lustrous. In section the xerogel coating thickness was in the region of 1 to 30 μm. When scratching the surface with a dental probe, drag indentation marks were left.

Thicker coatings were produced by multiple deposition of gel and xerogel. Xerogels derived from multiple gel or gel-xerogel-gel layers could not be distinguished as individual layers with SEM analysis. The multiple coated surface appeared as a single coating. Up to 3-4 coats could be applied, and above this number severe surface crazing resulted.

The polymeric gel state requires heat treatment to produce the collapsed molecular structure free of pores and organic residues, that is a glass. Clinical applications require the heat treatment process to avoid vital tissue. Three methods of heat treatment were tried:

(i) cw IR laser radiation at 1.06 μm (cw=continuous wave)

(ii) cw IR laser radiation at 10.6 μm (iii) Butane gas flame (i) 1.06 μm Laser

Continuous wave Nd:YAG laser radiation, powers up to 20 W, did not consolidate the sol-gels. This was due to very low absorption of the 1.06 μm radiation. In order to enhance absorption the sol-gel was modified by the addition of dissolvable transition ion salts as In Examples 1 and 2.

As a consequence of high temperature rises the high energy input resulted in the tooth becoming hot to handle and the tooth enamel tended to fracture. These trials were performed on extracted teeth, not in vivo.

(ii) 10.6 μm Laser

Warm air dried (60√-70° C.) sol-gels of 1% concentration in silica, applied by dip-coating, were consolidated on the tooth surface at low irradiance (40-100 W/cm$^2$) at exposure durations of 100 ms to 1 s. Multiple laser exposures (2-3 at 1 Hz) were necessary to consolidate the gel fully, the surface appearing lustrous and transparent to the naked eye. Scanning electron micrography revealed the surface to be smooth and featureless but with an appreciable degree of fracture. A crimped surface pattern was common in pits and fissures.

When a consolidated surface was scratched with a dental probe the surface fractured like glass. Clean, well defined edges were produced. The consolidated surface appeared smooth and featureless and no pores were detected at a 1 μm resolution. The following cw CO$_2$ laser parameters were found to produce good consolidated glass with minimal film cracking and without any damage to the tooth detectable by scanning electron microscopy:

cw Laser Power: 5 to 6 W ⎫
Exposure duration: 0.8 s ⎬ = 4.0 to 4.8 W
Pulsing rate: 1 Hz ⎭     ⎫ about $\frac{1}{3}$-$\frac{2}{3}$
Number of exposures: 2-3    ⎬ W/mm$^2$
Spot size: 3-4 mm diameter ≈ 7 to 12 mm$^2$ ⎭

Excessive laser heat treatment by means of higher irradiance (greater than approximately 150 W/cm$^2$) and or multiple laser exposures (4-6 pulses, 1-2 Hz, at 100 ms to 5 sec) produced excessive crazing and cracking and blistering of the coating.

One successfully used laser was a continuous wave CO$_2$ laser emitting a maximum output of 20 W at 10.6 μm, whose beam was focussed such that the spot size was (0.2 mm)$^2$ and whose beam was scanned on the substrate in zig-zag mode, such that the spot traversed its own diameter in 0.1 milliseconds while advancing steadily at such a rate that after one complete zigzag (1 cycle) it had returned to an area exactly abutting its original location. In this way, every point on the tooth surface received two and only two periods of illumination, each lasting 0.1 ms. It was found preferable to illuminate each point twice rather than once (even when the total energy input per unit area was the same), and scanning modes allowing four or six separate periods of illumination have also been successful. This procedure consolidated the sol gel and yielded a serviceable coating.

The following optional enhanced procedure was carried out experimentally on extracted human teeth for sol-gel consolidation followed by fusion vitrification and was found to be advantageous in generating a good subsurface vitreous structure without adverse thermal and mechanical defects to the tooth as a whole:

The tooth was dip coated and allowed to drip dry on adsorbent paper and or warm air dried.

The surface of the tooth was then scanned using the above laser scanning parameters, but at a low power (below 5 W). This is to gently warm the sol-gel thin film and evaporate solvents and water. The surface may be scanned several times; 2–5 scans is normally sufficient (dependent upon the solvent/water content of the gel).

The power is increased to 8–12 W to fully consolidate the gel to a glassy film. Several (two to four) scans may be necessary. If the <5 W procedure is not followed then the gel is vaporized/ablated from the tooth surface whereby subsequent vitrification of the enamel surface will contain only small amounts of silica.

This yields a firm glassy film on unmodified tooth, which may be adequate.

The laser output power may now however be further increased (9–18 W, spot size is critical again) and scan parameters reduced to 6mm×6 mm area (=tooth area) so as to attain high enough energy delivery per unit area to a level where the tooth subsurface is vitrified and the glassy film becomes incorporated into the new resultant vitreous enamel substance.

The power input to the sol gel is preferably 25 to 500, e.g. 40 to 250 W/cm$^2$, and may be higher as long as the substrate be not damaged; the energy input per period of illumination is preferably at least 1 J/cm$^2$, more preferably at least 10 J/cm$^2$.

An alternative laser, avoiding the problems of scanning, has a large spot (as large as the tooth, whose environs would be masked); this is the transversely excited atmospheric laser.

Multiple thin films could be built up by consolidation of individual gel layers. The resultant coating also tended to be fractured through the full thickness of the coating. The individual layers of glass were only distinguishable when the surface was scratched. However, the glass-glass boundary appeared to be continuous with the absence of gaps.

(iii) Butane

The temperature of butane ($CH_3CH_2CH_2CH_3$) gas burning with a blue flame (approaching complete combustion to $CO_2$ and $H_2O$) is near 1000° C. Exposing a material surface of negligible heat capacity, such as sol-gel glass coatings of 10 μm thickness, may cause surface temperature rises in the region of 800° to 1000° C. Such temperatures may be used to consolidate the "gel" state to a glass. The associated events would be initial evaporation and combustion of organic residues, accompanied by simultaneous collapse of the $SiO_2$ structure to a glass monolith.

Sol-gel coated specimens were, momentarily, exposed to the blue part of a butane bunsen flame. The specimens were moved horizontally through the flame at a rate of 6–8 cm/s for 2–4 s. The specimens became warm but not hot to the touch.

Sol-gel coatings on enamel, dentine, restorative materials, silicon wafer substrates and glass slides could all be consolidated to a glassy film without excessive heating. The consolidated glassy film was smooth and featureless with little cracking. However, at longer flame exposure durations (approximately 3–6 s) or slower rate of traverse through the flame (less than 6 cm/s), severe film cracking resulted with flaking and blistering of the glassy coating. Specimens of teeth become warm, but not hot to the touch, during the brisk flame consolidation.

In appearance the converted film was similar if not identical to that produced by consolidation with the $CO_2$-laser heat-treated sol-gel.

These cured sol-gel coatings were then subjected to 'accelerated attack', namely exposure to 0.5M lactic acid at 37° C. for 30 days.

Flame-consolidated films on glass slides and on silicon wafers lost 20% of their weight and the physical appearance changed becoming opaque (with possible precipitation of $SiO_2$ and or break down of polymeric structure). However, improved results were obtained using 5 seconds' exposure to 1100° C. $CO_2$-laser consolidated films as set forth above remained transparent at all times and did not dissolve. Continuous wave $CO_2$ laser irradiation for 100–500 ms on a spot size of 2 mm diameter (corresponding irradiance 200 W/cm$^2$) was also found to consolidate silica sol-gel films. The laser beam in the chopped mode (20 Hz, 25–45 ms pulse duration) could also consolidate sol-gel coatings to a lactic-acid-resistant glass. Xerogels cured for 10 hours or more did not lose weight and remained transparent. This applied also to exposure for 16 weeks to 0.5M lactic acid, or exposure to fuming nitric acids, or to 30% orthophosphoric acid (=dental etchant). The films were resistant to scratching by anything other than a diamond burr.

In de-ionised water, the bulk of flame-consolidated sol-gel films remained unchanged. However, their surface layer became opaque and white; xerogels remained transparent.

Organic solvents such as ethanol, propanol, ethanone, or methoxymethane were found not to dissolve either the flame consolidated coatings or the xerogel. The coated surface remained smooth and featureless.

An accelerated wear test using a toothbrush weighted to 360 g rubbing the $CO_2$-laser-consolidated sol-gel coating under water at 190 strokes per minute removed about 95% of the coating after 24 hours. From this, assuming that normal brushing occurs for 20 seconds daily on each surface, a coating life of about 12 years may be expected, as a very approximate guide.

EXAMPLE 5

This preparation took place under dry nitrogen. Except as stated, no solvents were used.

Tetraethoxysilicate liquid (25 g) was placed In a vessel, to which 5 g tetra-sec-butoxy titanium liquid was added with stirring. The mixture was a stable liquid. Then 4.5 g ethoxysodium solid was dissolved in the mixture, yielding a yellow/orange liquid.

Then 5 g trisecbutoxy aluminium liquid were added with stirring. A solid gel-like mass precipitated immediately. When this has happened in the past, it has been customary to throw the sample away as a failure. However, we have surprisingly found that the situation can be rescued and, Indeed, that this precipitation stage is positively advantageous, because the solid can be stored indefinitely airtight under dry nitrogen or even dry air.

When required, therefore, the solid is allowed controlled access to atmospheric moisture, which exposure also permits controllable loss of mixed alcohols arising from hydrolysis of the various alkoxy groups present. A stable liquid sol-gel results. This can either be converted into a non-glassy (non-clear) xerogel, or it can be diluted tenfold using a non-alcoholic (i.e. non —OH group containing) solvent, such as acetone $(CH_3)_2CO$ or diethyl ether $(C_2H_5)_2O$. To that diluted sample, we add a pure-silica sol gel made in acetone and then partially hydrolysed, to the extent of two water molecules per silicon atom. This mixture is quickly applied as a coating (or otherwise placed where desired), and within a few minutes it gels and may be converted to a clear glassy xerogel by slow drying in air at room temperature.

EXAMPLE 6

Objective: Observe effect of ageing (limited access to atmospheric moisture)

Conditions: anhydrous $N_2$ atmosphere in air bag.

| Components: | Theoretical | Used |
|---|---|---|
| Na ethoxide | 17.6 g | 18.5 g |
| TEOS | 100 g | 101 g |
| Al tri-sec-butoxide | 15.6 g | 16.0 g |

Al-sec butoxide was first dissolved in TEOS (tetraethoxysilicon) followed by Na-ethoxide which results in a white suspension/precipitate. This was stirred for 3–4 hours and although the stirrer becomes slightly warm this appears not to dissolve the precipitate. However the sol-gel and precipitate become darker orange-brown from the initial pale orange colour.

Restricted access to atmospheric moisture: 96 hr later (in air bag) the sol-gel system becomes a viscous orange-brown suspension/precipitate.

The exposure of the sol-gel material to atmospheric moisture leads to a degree of hydrolysis which in many other cases, but not here, would have produced a clear sol-gel liquid. Therefore the system was filtered and the filtrate liquid studied.

(In subsequent Examples, the same procedure was followed, that is, if exposure to atmospheric moisture failed to redessolve the whole system, it was filtered and the filtrate was sealed and stored for later use.)

The above filtered liquid sol-gel was exposed to atmospheric moisture (for 24–48 hours) so as to induce gelling/formation of a xerogel. A crumbly orange solid resulted.

The residue from the above sol-gel was also analyzed for its percentage oxide content. The slurry was heated to drive off organics at 500° C.; a grey solid results.

| | Differential Scanning Calorimetry (DSC) | | Thermogravimetric Analysis (TGA) wt loss to 850° C. |
|---|---|---|---|
| | Endotherm Peak Temp | Area | |
| Xerogel | 112° C. | 210 J/g | 29.7% |
| Residue heated to 500° C. | 64° C. | 14.8 J/g | 4.0% |

| Percentage Oxide Analysis by mass (by atoms of Si + Al + Na = 100 in brackets) | | | | |
|---|---|---|---|---|
| | $SiO_2$ | $AlO_{1.5}$ | $NaO_{0.5}$ | Loss on Ignition at 800° C. |
| Xerogel | 59.9% (78.1%) | 4.3% (6.6%) | 6.1% (15.3%) | 29.7% |
| Residue heat-treated to 500° C. | 40.6% | 11.7% | 43.7% | 4% |

The percentage oxide in the xerogel derived from the sol-gel contains only a fraction of the Na that is introduced via Na-ethoxide. The majority of the Na-ethoxide does not dissolve into the TEOS but remains as raw Na-ethoxide until moisture converts it to NaOH. There appears to be a high percentage of Al in the residue. This is possibly due to the formation of aluminium tetra-ethoxide through alcoholsis.

EXAMPLE 7

The aim was to assess the affect of slow atmospheric moisture on a prepared solidified sol-gel containing titanium, Conditions: anhydrous $N_2$ atmosphere in air bag.

| Components: | Theoretical |
|---|---|
| Na ethoxide | 4.4 g |
| TEOS | 25 g |
| Al tri-sec butoxide | 3.9 g |
| Ti tetra-isopropoxide | 4 g |

The order of addition was reversed: Na+TEOS (O.K.)+Ti isopropoxide (O.K.) but, when the Al-sec-butoxide is added immediately gelling/suspension/precipitation occurs (orange/yellow). The precipitate is thought to be Al-propoxide. Action: propanol from Ti-isopropoxide may be responsible, therefore the Al-sec butoxide needs to be added to Ti propoxide or use the higher order Ti-butoxide.

| | Molar Ratios: | | |
|---|---|---|---|
| Na Ethoxide | 4.4 g | (mw 68.05) | 0.065 moles |
| TEOS | 25 g | (mw 208.33) | 0.12 moles |
| Al tri-sec-butoxide | 3.9 g | (mw 246.33) | 0.0158 moles |
| Ti tetra-isopropoxide | 4 g | (mw 284) | 0.014 moles |

37.3 g of the above sol-gel would yield 11.935 g of solid oxide having a percentage yield of 32% w/w and a theoretical oxide composition by mass of 16.8% $NaO_{0.5}$+60.3% $SiO_2$+13.5% $AlO_{1.5}$+9.4% $TiO_2$.

The filtrate remained a stable liquid when stored airtight at room temperature for two years.

The above sol-gel was exposed to the atmosphere for 72 hours in a fume cupboard with a steady draught. This resulted in the formation of a white crust below which a meniscus of yellow/orange liquid also appeared. The rest of the sol-gel remained as a semi-solid. A further 24–48 hours later the amount of liquid increased until the solid became totally transformed to a liquid sol-gel. A surface crust formed during semi-solid to liquid transformation. Thermal analysis showed:

| | DSC | | TGA wt loss to 850° C. |
|---|---|---|---|
| | Endotherm Peak Temp | Area | |
| Surface crust | 112° C. | 415 J/g | 24.3% |
| Xerogel | 123° C. | 419 J/g | 25.4% |

| Percentage Oxide Analysis by mass (by atoms of Si + Al + Na + Ti = 100 in brackets) | | | | | |
|---|---|---|---|---|---|
| | $SiO_2$ | $AlO_{1.5}$ | $NaO_{0.5}$ | $TiO_2$ | LOI 800° C. |
| Surface Crust | 50.2% | 5.9% | 10.7% | 8.9% | 24.2% |
| Xerogel | 45.1% (53.0%) | 7.1% (9.7%) | 12.8% (29.0%) | 9.5% (8.3%) | 25.4% |
| Anticipated | 60% | 13.5% | 16.8% | 9.4% | — |

The surface crust was expected to contain a high percentage of Ti but, it appears there is little difference between the xerogel from the liquid sol-gel and the crust formed during semi-solid to liquid transformation.

Comparisons between anticipated yield and actual yield are similar in some respects. The Ti is as calculated. The amounts of Si, Al and also Na differ. These anomalies are due to loss of alkoxides into the atmosphere and also into the crust. The aim would remain to synthesis the four component sol-gel via a direct route omitting the semi-solid to liquid transformation stage.

EXAMPLE 9

| Components: | Theoretical | Used |
|---|---|---|
| Na Ethoxide | 4.4 g | 9 g |
| TEOS | 25 g | 51 g |
| Al tri-sec-butoxide | 3.9 g | 8.65 g |
| Ti tetra-iso-propoxide | 4 g | 8.5 g |

Conditions:
Dry $N_2$ atmosphere in air bag.

The sol-gel undergoes gelling when Al-sec butoxide is added to TEOS containing Na ethoxide and Ti iso-propoxide. Limited access of the solid gel to atmospheric moisture leads to solid to liquid transition. Excess dilution (>x 100) in laboratory ethanol leads to gelling (10 to 30 minutes' gelling time). Thin films can be produced. The wettability of this sol-gel in glass slides was poor. Thermal analysis of the xerogel showed:

| | Percentage Oxide Analysis (Atomic in brackets) | | | | LIO 800° C. |
|---|---|---|---|---|---|
| | $SiO_2$ | $AlO_{1.5}$ | $NaO_{0.5}$ | $TiO_2$ | |
| Xerogel | 46.3% (55.6%) | 5.7% (8.2%) | 12.3% (28.9%) | 8.0% (7.3%) | 27.7% |

DSC Endotherm peak temperature = 112° C. Area under peak = 391 J/g
TGA Weight loss to 850ÅC = 27.7%

EXAMPLE 9

Conditions: anhydrous $N_2$ atmosphere In air bag.

| Components: | |
|---|---|
| Na ethoxide | 18 g |
| TEOS | 100 g |
| Al tri-sec-butoxide | 17 g |

Procedure:
Order of addition: Al tri-sec-butoxide into TEOS then Na ethoxide into this.

Aluminium tri-sec-butoxide, a clear viscous liquid, dissolves with ease in TEOS. On addition of Na ethoxide, a fine yellow powder, at first it does not appear to dissolve readily. Approximately 10–15 minutes later a yellow tint in the sol becomes apparent and the undissolved powder settles out. 12 hours later, still in $N_2$ atmosphere, the sol becomes intensely dark brown with also a dark brown semi-gelatinous residue.

With time (12–24 hr later) the Na ethoxide appears to produce an intensely brown coloured sol and there is a distinct absence of the characteristic odour of TEOS. On filtering, a brown coloured liquid results which is strongly alkaline—pH about 10–11.

The inference from the above is that, on stirring vigorously, a small quantity of Na-ethoxide dissolves in the sol producing the intense brown coloration, and the loss of TEOS odour suggests that hydrolysis has taken place in the strongly alkaline conditions. Note also that the addition of ethanol to Al tri-sec-butoxide causes an instantaneous precipitation of a white semi-gelatinous material. This is thought to be Al-tri-ethoxide.

The addition of Na ethoxide to TEOS first followed by Al-sec butoxide makes no difference.

Exposure of sol-gel to atmosphere with limited access (so as to age it) causes no difference in the appearance. This neat, aged, sol-gel produces a film on glass slides but it is discontinuous, white and flaky.

Dilution of the sol gel by a factor of 8 with ethanol (introduces a degree of water) has no effect upon the sol-gel. This suggests the Al tri-sec-butoxide has been hydrolysed and undergone sufficient polycondensation so as not to be affected by the addition of ethanol. Thin films may be formed. The quality of the film is variable according to film deposition conditions.

The time for which the sol-gel ages is also important, because the degree of polycondensation is related to viscosity and wettability.

| | Analytical Data | | TGA |
|---|---|---|---|
| | DSC | | |
| | Endotherm Peak Temp | Area | wt loss to 850° C. |
| Xerogel | 117° C. | 266 J/g | 26.8% |

EXAMPLE 10

| TEOS | 21.9 g |
|---|---|
| Na ethoxide | 4.7 g |
| Zr tetra-isopropoxide | 4.3 g |

Na ethoxide+TEOS, Na ethoxide does not fully dissolve. To this mixture Zr propoxide was added (no adverse reaction). This solution/solid mixture was filtered. The filtrate is stable in air at room temperature and pressure and humidity. The residue is thought to contain undissolved Na ethoxide.

| | Percentage Oxide Analysis (Atomic in brackets) | | | LOI 800° C. |
|---|---|---|---|---|
| | $SiO_2$ | $NaO_{0.5}$ | $ZrO_2$ | |
| Xerogel | 48.6% (59.9%) | 13.9% (33.3%) | 9.9% (7.1%) | 27.6% |

EXAMPLE 11

The following components were mixed:
Na ethoxide 21.5 g
TEOS 104.05 g
Al sec-butoxide 17.4 g
Ti tetra-isopropoxide 20.42 g After a year's storage at −10° C., this was found to have separated into a clear viscous liquid above a semi-solid phase. Such samples would normally be rejected, but we have discovered that this is unnecessary. The liquid can successfully be used in its own right and may be loaded with filler, or else the sample can be allowed limited access to moisture at room temperature (e.g. by providing apertures in the seal), when it will be found that after a day or so the liquid becomes less viscous and eventually dissolves all the semisolid phase, yielding a stable sol-gel liquid. The separation can be entirely avoided by exposing the freshly prepared mixture to room humidity for 2–3 weeks and then sealing it; such a sample has remained a stable liquid for over a year.

EXAMPLE 12

The object was to make a solventless sol-gel, of intended composition (by weight): $SiO_2$ 60.3%; $Na_2O$ 16.83%; $Al_2O_3$ 13.3%; $ZrO_2$ 9.4%

The following components were assembled:

|  | Calculated | Used |
|---|---|---|
| TEOS | 98 g | 99.62 g |
| Zr tetra-sec-butoxide | 13.875 g | 13.79 g |
| Al tri-sec-butoxide | 16.01 g | 19.87 g |
| Na ethoxide | 9.2 g | 9.3 g |

The following procedure was carried out in a dry nitrogen atmosphere. The TEOS and Zr salt (a yellow viscous liquid) were mixed and readily yielded a stable clear yellow liquid. The Al salt was added, resulting in a white precipitate/suspension, which may consist of Al triethoxide (which can form from the components present). The Na ethoxide, a yellow powder, is added and mixed for one hour, and, after settling, results in a clear liquid above a semi-transparent viscous orange layer, the lower part of which is gelatinous, above a layer of white granules. This is not a clear usable sol-gel!

However, after exposure of this to limited atmospheric moisture for 19 days, the mixture unexpectedly becomes totally clear, even the granules being resorbed, yielding a slightly viscous orange-tinted sol-gel, which, if left fully open to the atmosphere, eventually turns into a glassy xerogel. Mica was added immediately after the sodium ethoxide.

EXAMPLE 13

Somewhat akin to the foregoing example, a $SiO_2$+Zr+Al+Na+Ti sol-gel was made up using the following ingredients: TEOS 12.27 g (actual); Zr tetra-sec-butoxide 1.70 g; Al-tri-sec-butoxide 2.45 g; Na ethoxide 1.14 g; and Ti isopropoxide 6.1 g. To a mixture of the TEOS and the Zr salt, the Al salt was added with mixing, then the Na salt. After 1 hour's agitation, a viscous yellow-orange suspension resulted, to which the Ti salt was added with no ill effects; the mixture remained a suspension but also some material settled out as In the previous example. After 2–3 weeks' exposure to limited atmospheric moisture, a clear sol-gel liquid resulted, which is considered likely to remain stable for at least a year when stored either at −10° C. or at room temperature, under sealed conditions. This liquid produces a glassy xerogel.

In an experiment, the Al tri-sec-butoxide was replaced by Al-tri-propoxide, which gave inferior results, possibly because It (the propoxide) was faster reacting, leading to faster hydrolysis and hence more undesirable precipitation.

I claim:

1. A sol gel, xerogel or heat-consolidated gel composition comprising a hydrolysable silicic ester, a solvent, and alkoxides of: a GpIA metal, and of: any one, two or more of Al, a GpVB metal and a GpIVB metal.

2. A composition according to claim 1, wherein the silicic ester is silicon tetrahalide or tetraalkoxysilicon.

3. A composition according to claim 1, wherein the GpIA metal is sodium.

4. A composition according to claim 1, wherein the GpIVB metal is titanium.

5. A composition according to any of claim 1, wherein the metal alkoxides are: (i) Al, Ti, Na; or (ii) Zr, Na.

6. A composition according to claim 1, further comprising a filler.

7. A composition according to claim 6, wherein the filler comprises up to the 30% by weight of the composition before curing.

8. A composition according to claim 6, wherein the filler is in the form of flat plates.

9. A composition according to claim 8, wherein the filler comprises talc or mica.

10. A composition according to claim 6, wherein the filler comprises laponite, zeolite, kaolinite or vermiculite.

11. A composition according to claim 6, wherein the filler is coated.

12. A composition according to claim 11, wherein the filler is coated with any ones two or more of titanium dioxide, chromium oxide and ferric oxide.

13. A composition according to claim 6, the mean filler particle size is up to 3 μm in one dimension and 5–100 μm in the other two dimensions.

14. A composition according to claim 1, wherein the composition comprises water and wherein the molar proportion of water:silicon is (1 to 4):1.

15. A composition according to claim 1, wherein the solvent comprises a ketone or alcohol.

16. A composition according to claim 1, wherein, taking atoms of Si+GpIA+Al+GpIVB+GpVB as 100, silicon is at least 30.

17. A composition according to claim 16, wherein GpIA is under 50.

18. A composition according to claim 16, wherein Al is from to 15.

19. A composition according to claim 16, wherein Al+GpVB+GpIVB together is from 3–15.

20. A composition according to claim 16, wherein Al+GpVB+GpIVB together does not exceed one-sixth of the silicon.

21. A composition according to claim 1, further comprising a non-metallic glass former (other than Si).

22. A composition according to claim 1, during the synthesis of which an ageing step comprised admitting moisture to the composition at a rate under 1% of the rate in free air.

23. A process for producing a glassy coating, comprising applying a composition according to any preceding claim to an object to be coated, and curing the coating.

24. A process according to claim 23, wherein the coating as applied (before curing) is up to 30 μm thick.

25. A process according to claim 23, wherein the coating is cured by an energy input of 2–10 $J/mm^2$.

26. A process according to claim 23, wherein the coating is cured by energy supplied at a rate of under 4 $W/mm^2$.

27. A method for cosmetic colouring of a tooth, comprising performing a process according to claim 23, wherein said object is the tooth and wherein: the composition includes a pigment; or a said filler is present and is formulated to appear a tooth-like colour in the applied thickness; or a cosmetic stain is applied to the tooth prior to applying the said composition.

28. A method for prophylactic protection of a tooth, comprising performing a process according to claim 23, wherein said object is the tooth.

29. A method according to claim 28, wherein a said filler is present and is so formulated as to appear a tooth-like colour in the applied thickness.

30. A process according to claim 23, wherein said object is a patient's tooth.

* * * * *